United States Patent [19]
Clegg et al.

[11] Patent Number: 5,755,563
[45] Date of Patent: May 26, 1998

[54] PUMP WITH LOCK-OUT FEATURE

[75] Inventors: Robert D. Clegg, Pickerington; Matthew S. Fleming, Columbus; Clark E. Fortney; Robert S. Osborne, both of Gahanna, all of Ohio

[73] Assignee: Abbott Laboratories, Abbott Park, Ill.

[21] Appl. No.: 625,684

[22] Filed: Apr. 3, 1996

[51] Int. Cl.[6] .................. F04B 43/09; F04B 49/00
[52] U.S. Cl. ........................... 417/326; 604/65
[58] Field of Search ..................... 417/326, 15, 42, 417/43, 53, 477.1; 604/65-67

[56] References Cited

U.S. PATENT DOCUMENTS

| | | | |
|---|---|---|---|
| 4,213,454 | 7/1980 | Shim | 606/65 |
| 4,634,426 | 1/1987 | Kamen | 604/65 |
| 5,041,086 | 8/1991 | Koenig et al. | 604/65 |
| 5,181,910 | 1/1993 | Scanlon | 604/65 X |
| 5,630,710 | 5/1997 | Tune et al. | 417/326 |
| 5,658,250 | 8/1997 | Blomquist et al. | 604/65 |

FOREIGN PATENT DOCUMENTS 2118333  10/1983  United Kingdom ............ 604/65

Primary Examiner—Ismael Izaguirre
Attorney, Agent, or Firm—Brian R. Woodworth

[57] ABSTRACT

An apparatus and method for controlling a flow parameter of a pump. The pump includes a pumping device for pumping fluid, the pumping device having at least one flow parameter. The pump further includes a control coupled to the pumping device and a control panel having a plurality of controls operable by a human. The control is programmable by operation of the plurality of controls, thereby allowing a human to program the at least one flow parameter of said pumping device by operation of the plurality of controls. The control has a lock that can be activated by operation of at least two of the plurality of controls. Upon activation, the lock prevents the alteration of the at least one flow parameter. The method includes the step of providing the pump of the present invention, programming the at least one flow parameter by operating the plurality of controls, and activating the lock by operating at least two of the plurality of controls.

9 Claims, 3 Drawing Sheets

PUMP WITH LOCK-OUT FEATURE

BACKGROUND OF THE INVENTION

The present invention is directed to a pump for introducing enteral or parenteral fluids into the body of a patient. More particularly, the present invention is directed to a pump having a lock feature that enables a pump operator to prevent unauthorized or inadvertent changes to the pump operating parameters selected by the operator.

A variety of pumps are used in a number of medical applications, including the infusion of parenteral and enteral fluids into a patient. For example, peristaltic pumps such as the Flexiflo® III enteral pump distributed by Ross Products, a division of Abbott Laboratories, are used to infuse enteral fluids into a patient in order to provide nourishment. Many of the pumps currently used for the infusion of enteral and parental fluids are programmable, thereby enabling an operator to establish certain operating parameters for the pump. For example, the pump may be programmable to run for a selected period of time at a selected rate, thereby enabling the operator to attend to other duties rather than monitoring the infusion process. The pump also may be programmable to permit the operator to select other infusion parameters such as the volume of infusate delivered to the patient.

There is a risk that pump operating parameters, once programmed into the pump, can be changed as a result of inadvertent contact with the pump or as a result of purposeful, unauthorized tampering. For this reason, lock features have been provided on some pumps. Such lock features enable the pump operator to program the desired infusion parameters and then "lock" the pump, i.e., prevent changes to the infusion parameters, by using a key to lock and unlock the pump. Such "keyed" lock systems can be impractical in many applications. For example, a patient in a hospital typically is attended by a number of doctors, nurses, and medical technicians, each of whom may wish to reprogram the infusion parameters during operation of the pump. It is highly possible that a key will become misplaced under these circumstances due to the number of persons needing access to the same key. As a result, these medical professionals may have to waste valuable time seeking out a key in order to effect changes to the pump's flow parameters. It is desirable to provide a pump having a keyless lock feature, thereby obviating the need for a key and eliminating the problems associated with such keyed systems.

SUMMARY OF THE INVENTION

The present invention provides a pump and a method for controlling at least one flow parameter of a pump. The pump of the present invention includes a pumping means for pumping fluid. The pumping means has at least one programmable flow parameter. The pump further includes a control means for controlling the pumping means, the control means being coupled to the pumping means. A control panel is coupled to the control means. The control panel has a plurality of controls operable by a human, the control means being programmable by operation of the controls on the control panel, thereby enabling a human to program at least one programmable flow parameter of the pumping means. The control means further includes a lock that is activated by operation of a plurality of the controls on the control panel. The control means prevents alteration of the at least one flow parameter when the lock is activated.

The method of the present invention includes the step of providing a pump constructed in accordance with the present invention. The method further includes the step of programming the at least one flow parameter of the pumping means by operating the plurality of controls. The method also includes the step of activating the lock by operating the plurality of controls, thereby preventing alteration of the at least one flow parameter of said pumping means until said lock is deactivated.

BRIEF DESCRIPTION OF THE DRAWINGS

For a more complete understanding of the present invention, reference may be had to the following Detailed Description read in connection with the accompanying drawings in which.

DETAILED DESCRIPTION

Figure 1:
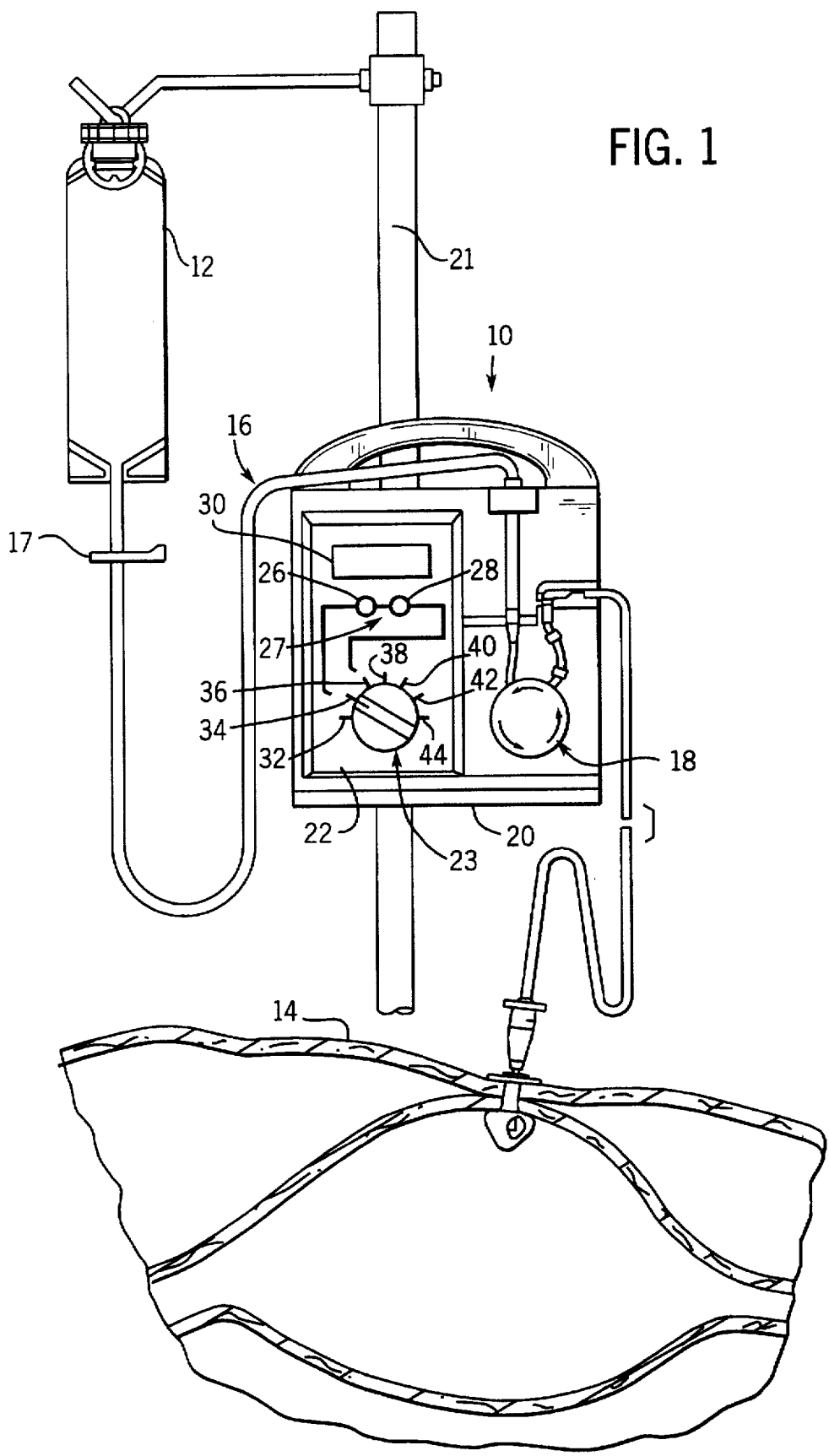
FIG. 1 is a perspective view of a pump constructed in accordance with the present invention utilized to infuse enteral fluids into a patient.
Figure 2:
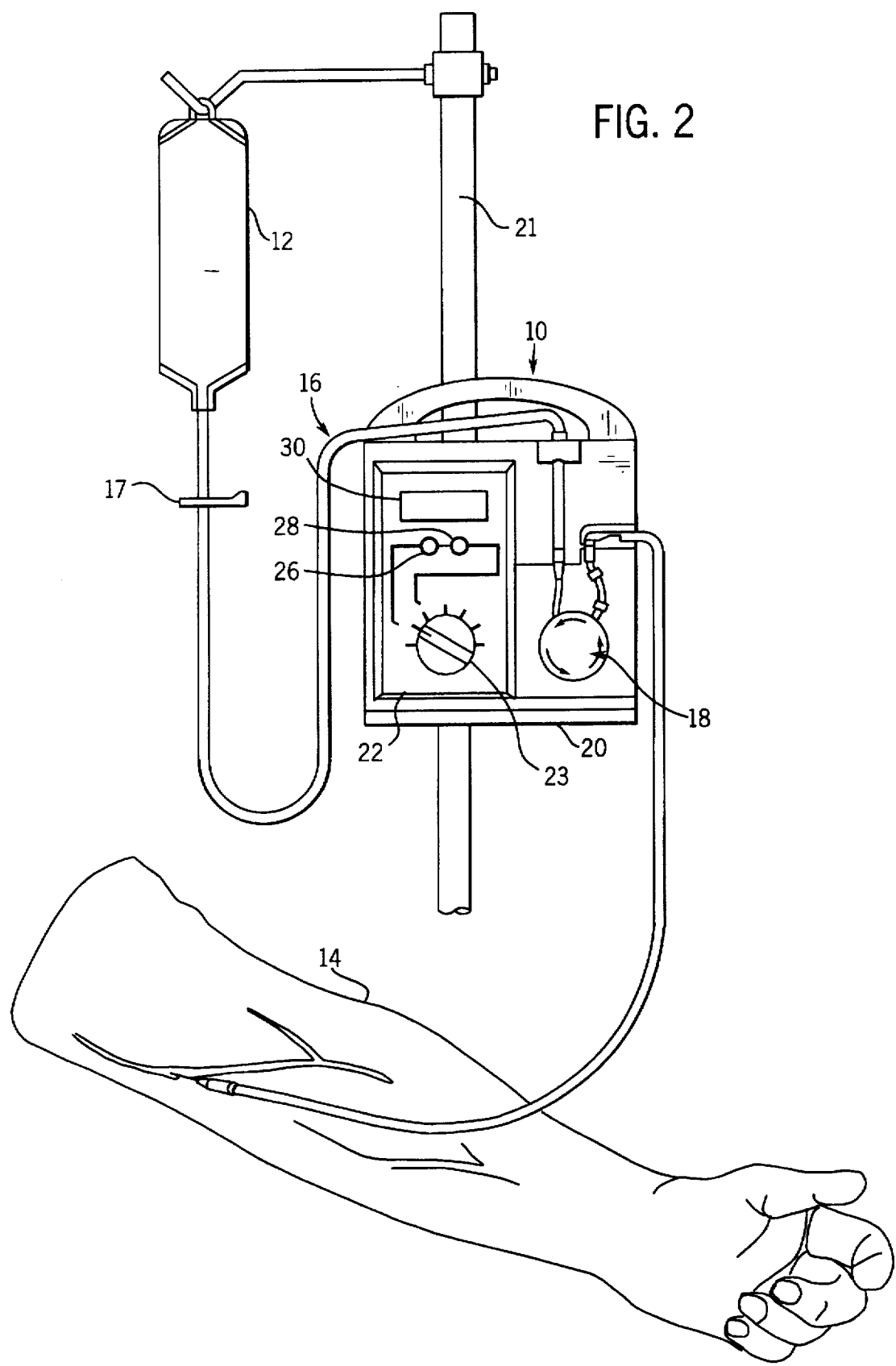
FIG. 2 is a perspective view of a pump constructed in accordance with the present invention utilized to infuse parenteral fluids into a patient.

A pump constructed in accordance with the present invention is generally indicated at 10 in FIGS. 1 and 2. Pump 10 can be utilized to deliver enteral fluids (as depicted in FIG. 1) or parenteral fluids (as depicted in FIG. 2) from a reservoir 12 to a patient 14 through tubing 16. It is to be appreciated that pump 10 can be used to introduce enteral fluids to a patient through a nasogastric tube, i.e., an enteral feeding tube passed through the nose and into the stomach, as well as through a gastrostomy as tube depicted in FIG. 1. Although the discussion set forth herein with respect to pump 10 of the present invention is directed to the configurations depicted in FIGS. 1, 2, and 3, one of ordinary skill in the art will appreciate that other enteral and parenteral applications are within the scope of the present invention, as claimed in the appended claims.

Pump 10 includes a pumping means 18 mounted on pump housing 20. The pumping means 18 depicted in FIGS. 1 and 2 is a peristaltic pump of known construction. However, pumping means 18 can be any of a variety of known types of pumps, including, but not limited to, piston pumps, peristaltic pumps (linear and non-linear), diaphragm pumps, and scroll pumps. The selection of an appropriate pumping means for use with pump 10 of the present invention will be dependent upon, inter alia, the viscosity of the solution (enteral or parenteral) being administered to the patient, the desired flow characteristics, and personal preferences of the operator and the responsible medical professional. In the preferred embodiment of the present invention depicted in FIGS. 1 and 2, pump housing 20 is configured to be mounted on stand 21. Stand 21 also is configured to retain reservoir 12 in a hanging position. A flow control device 17 is provided on tubing 16 in order to provide additional control of flow through tubing 16. Flow control device 17 can be a slide clamp, roller clamp, stop cock, or any other known flow control device.

Control panel 22 is provided on pump housing 20. In the preferred embodiment of the present invention, control panel 22 includes a plurality of controls, including an operational control generally indicated at 23 in FIG. 1. In the embodiment of the present invention depicted in FIGS. 1 and 2, operational control 23 comprises dial control 24. In the preferred embodiment depicted in FIGS. 1 and 2, dial control 24 has six positions: Off/Charge activated position 32, Set Rate (ml/hr) activated position 34, Set Dose (ml) activated position 36, Run (ml/hr) activated position 38, Hold activated position 40, Vol Fed (ml) activated position 42, and Clear Volume activated position 44. It will be appreciated by one of ordinary skill in the pertinent art that forms of operational control 23 other than dial control 24 can be used in connection with the present invention. For example, a push button control panel having a plurality of push buttons that correspond to the above-referenced positions of dial control 24 can be used in lieu of dial control 24. Alternatively, a slide bar having positions corresponding to each of the above-referenced activated positions of dial control 24 can be employed. Dial control 24 also can be replaced with a remote control device of known construction and operation. One of ordinary skill in the pertinent art will appreciate that various other equivalent forms of operational control 23 can be used in connection with the apparatus and method of the present invention.

Control panel 22 further includes increase control 26, decrease control 28, and display screen 30. In the preferred embodiment of the present invention depicted in FIGS. 1 and 2, increase control 26 and decrease control 28 make up a magnitude control generally indicated at 27 in FIG. 1. In the preferred embodiment, increase control 26 and decrease control 28 are push buttons. It will be appreciated by one of ordinary skill in the art that other types of magnitude control 27 can be used in connection with the present invention. For example, a dial control can be used in lieu of increase control 26 and decrease control 28, whereby the magnitude of a flow parameter can be increased by turning the dial control in a first direction and decreased by turning the dial control in a second, opposite direction. Alternatively, a slide bar can be used in lieu of increase control 26 and decrease control 28, whereby the magnitude of a flow parameter can be increased by sliding the slide bar in a first direction and decreased by sliding the slide bar in a second, opposite direction. One of ordinary still in the art will appreciate that additional forms of magnitude control 27 can be employed without departing from the spirit and scope of the present invention.

In the preferred embodiment of the present invention, dial control 24, increase control 26, and decrease control 28 are electronically coupled to microcontroller 106. Microcontroller 106 preferably controls all of the flow parameters produced by operation of pump 10. Such parameters include flow rate, flow volume, flow duration, and flow profile. Increase control 26 and decrease control 28 can be used to increase and decrease, respectively, a magnitude of a flow parameter stored in microcontroller 106. Microcontroller 106 then transmits a signal to display screen 30 which displays a digital or analog representation of the magnitude stored in microcontroller 106. In the preferred embodiment of the present invention, display screen 30 provides a digital display. Increase control 26 and decrease control 28 are preferably configured such that they can decrease and increase, respectively, the digital or analog display by a single unit when pressed and released, and such that they continually decrease and increase, respectively, the digital or analog display when pressed and held, thereby enabling an operator readily to select a desired magnitude for a given flow parameter or for operation of the hold feature. The operation of increase control 26 and decrease control 28 will be described in greater detail below with respect to the operation of pump 10.

The function and operation of dial control 24, increase control 26, and decrease control 28 when dial control 24 is in Off/Charge activated position 32, Set Rate (ml/hr) activated position 34, Set Dose (ml) activated position 36, Run (ml/hr) activated position 38, Vol Fed (ml) activated position 42, or Clear Volume activated position 44 are described in detail in the FLEXIFLO® PATROL™ Enteral Pump Operating Manual which is incorporated herein by reference. These features are included in the best mode of the invention disclosed herein. However, these features form no part of the invention claimed in the appended claims and therefore will not be discussed in detail herein. For a complete understanding of the best mode of the present invention, reference should be made to U.S. application Ser. Nos. 08/531,541; 08/531,674; 08/531,577; 08/531,687; 08/531,690; 08/531,874; and 08/532,030 filed on Sep. 21, 1995. These applications are incorporated herein by reference.

Alarm 46 is provided in pump 10. Alarm 46 can be a visual alarm, an audible alarm, or a combination visual/audible alarm. In the preferred embodiment of the present invention, alarm 46 provides both an audible alarm signal and a visual alarm signal on display screen 30. Alarm 46 is preferably electronically coupled to microcontroller 106. The operation of alarm 46 will be discussed in detail below.

Figure 3:
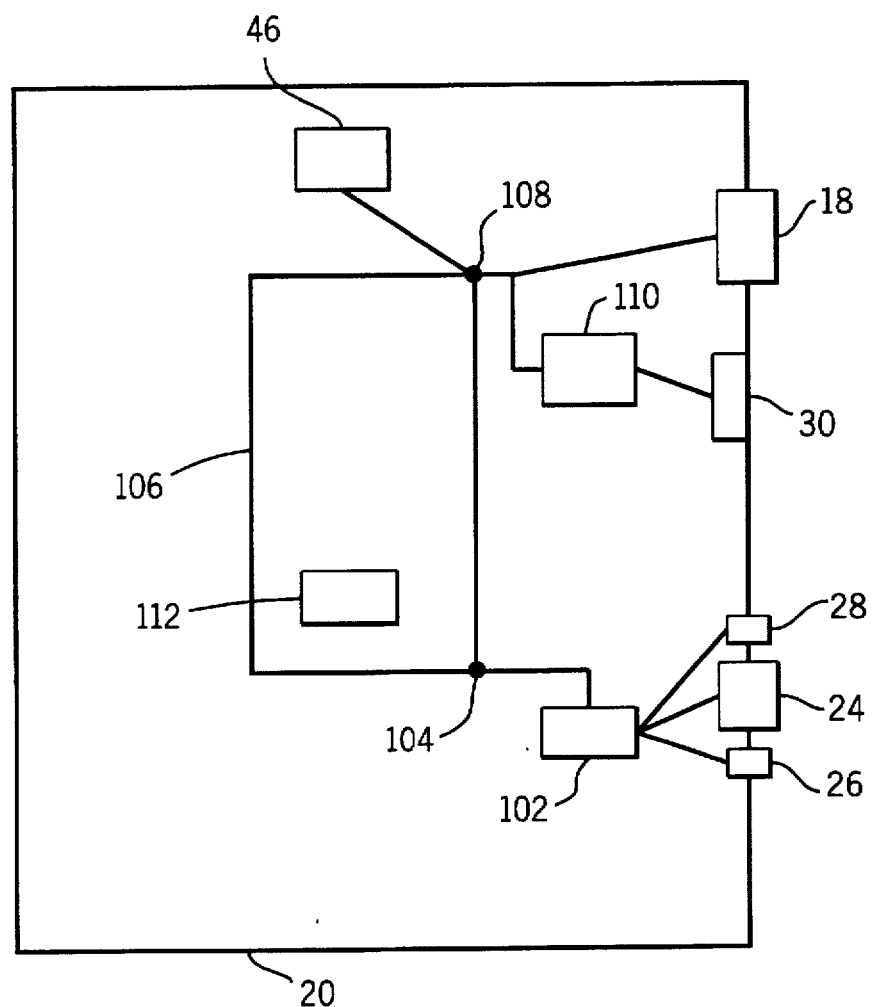
FIG. 3 is a schematic view of a pump constructed in accordance with one embodiment of the present invention.

In the embodiment of the present invention depicted in FIG. 3, operational control 23 is connected to Hall-effect sensors 102. Hall-effect sensors 102 are connected to input pins 104 of microcontroller 106. Microcontroller 106 preferably has a read-only memory capacity. Microcontroller 106 is programmed such that it can detect the position of operational control 23 by interpreting the output of Hall-effect sensors 102. Output port 108 of microcontroller 106 is connected to a display driver 110 which in turn is connected to display screen 30. Output port 108 of microcontroller 106 also is connected to and controls alarm 46. Microcontroller 106 preferably includes a timer subsystem 112 that enables microcontroller 106 to provide a countdown of the hold duration, as discussed in detail herein.

As above-discussed, magnitude control 27 is connected to microcontroller 106 which is programmed to sense the manual operation of magnitude control 27. When operational control 23 is in Hold activated position 40, magnitude control 27 can be used to set a hold duration in timer subsystem 112 of microcontroller 106 which then counts down from the set hold duration period, or the default duration period if no default duration is programmed. Upon expiration of the hold duration, microcontroller 106 activates alarm 46 and signals display driver 110 to activate an alarm signal on screen 30. In the preferred embodiment, timer subsystem 112, microcontroller 106, and display driver 110 work cooperatively such that display screen 30 displays the time remaining in the programmed hold duration as timer subsystem 112 counts down the selected/default hold duration. One of ordinary skill in the art will appreciate that various modifications can be made to these aspects of the present invention without departing from the intended scope of the invention as set forth in the appended claims.

When dial control 24 is in Hold activated position 40, microcontroller 106 disables pumping means 18. The disabling of pumping means 18 by microcontroller 106 can be produced by a variety of known methods, including an electronic disabling of pumping means 18, a mechanical disabling of pumping means 18, or a mechanical occlusion of the flow through tubing 16. In the preferred embodiment of the present invention, microcontroller 106 disables pumping means 18 by interrupting the flow of electrical energy to pumping means 18, thereby disabling pumping means 18 and interrupting the flow of fluid through tubing 16. In an alternative embodiment of the present invention, microcontroller 106 produces an electronic signal that disables pumping means 18. In a second alternative embodiment of the present invention, microcontroller 106 produces an electronic signal which causes a mechanical disabling of pumping means 18, e.g., the locking of the rotors of the peristaltic pump.

In the preferred embodiment of the present invention, microcontroller 106 and timer subsystem 112 have a default hold duration of five minutes. That is, when dial control 24 is placed in Hold activated position 40, microcontroller 106 assumes a default hold duration value of five minutes which is imparted to timer subsystem 112 of microcontroller 106. It will be appreciated that any default hold duration can be used in connection with the present invention. This default hold duration can be selectively changed by a pump operator through use of magnitude control 27, i.e., by selectively pressing increase control 26 and decrease control 28 in the embodiment of the present invention depicted in FIGS. 1 and 2 when dial control 24 is in Hold activated position 40. The hold duration can be programmable by seconds, by minutes, by hours, or by any combination thereof In the preferred embodiment of the present invention, the hold duration can be set in one minute intervals from one minute to ninety minutes. In the event that the operator of pump 10 is satisfied with the default hold duration, or upon completion of the programming of a selected hold duration, timer subsystem 112 and microcontroller 106 are set to activate alarm 46 and to signal display driver 110 to generate an alarm signal on screen 30 after pump 10 has been on "hold" for the hold duration. In the preferred embodiment of the present invention, microcontroller 106 and timer subsystem 112 return to the default hold duration each time dial control 24 is placed in Hold activated position 40. However, it will be appreciated that pump 10 can be modified such that the default hold duration is equal to the last programmed hold duration. Also in the preferred embodiment, display screen 30 displays both the hold duration in digital form and an indication that pump 10 is on "hold". Such an indication can be provided by displaying the word "hold" or the letter "H" on display screen 30 when dial control 24 is in Hold activated position 40.

Alarm 46 preferably can be manually deactivated. In the preferred embodiment of the present invention, alarm 46 is deactivated by rotating dial control 24 from Hold activated position 40 to any new position or by engaging magnitude control 27.

Pump 10 of the present invention preferably includes a lock feature that enables an operator to prevent inadvertent or unauthorized changes to flow parameters of pump 10 after the selected parameters have been programmed.. In one embodiment of the present invention, a means for preventing alteration of programmed flow parameters is incorporated into microcontroller 106. Such incorporation can be achieved using software or hardware. Activation of the lock feature of the preferred embodiment of the present invention is achieved by the simultaneous activation of two or more of the controls on control panel 22. In the preferred embodiment of the present invention, the lock feature is activated by simultaneously activating increase control 26 and decrease control 28 when dial control 24 is in Set Rate activated position 34. When dial control 24 is in Set Rate activated position 34, microcontroller 106 receives a signal from Hall-effect sensor 102 indicating that dial control 24 is in the Set Rate activated position. Simultaneous activation of increase control 26 and decrease control 28 sends a second signal to microcontroller 106, whereupon microcontroller 106 assumes a "locked" state in which the previously programmed pump operating parameters cannot be changed by further operation of operational control 23 and magnitude control 27. Microcontroller 106 also preferably signals display driver 110 to cause display screen 30 to display a "lock" indication, thereby confirming that microcontroller 106 is locked and informing the operator that pump 10 must be unlocked prior to effecting any changes to the flow parameters. In the preferred embodiment of the present invention, a "LOC" designation appears on display screen 30 when microcontroller 106 is in a locked state and dial control 24 is in Set Rate activated position 34, Set Dose activated position 36, or Clear Volume activated position 44. Also in the preferred embodiment of the present invention, microcontroller 106 can be unlocked by simultaneously activating increase control 26 and decrease control 28 when dial control 24 is in Set Rate activated position 34. Upon the unlocking of microcontroller 106, the "LOC" designation is removed from display screen 30 and the operator is free to make any desired changes to the flow parameters of pump 10.

It will be appreciated that various modifications can be made to the lock feature of pump 10 of the present invention without departing from the intended spirit and scope of the present invention as defined in the appended claims. For example, pump 10 can be configured such that a sequential or simultaneous activation of two or more controls, e.g., operational control 23 and magnitude control 27, causes microcontroller 106 to assume its "locked" state. In this modified embodiment, the same or a different sequential or simultaneous activation of two or more controls will unlock microcontroller 106. It will be appreciated that the locking of microcontroller 106 is preferably effected in accordance with the present invention by using the controls on pump 10, thereby obviating the need for an external key. In addition, it will be appreciated that the locking of microcontroller 106 is preferably effected using the controls of pump 10 in such a way that the procedure for unlocking microcontroller 106 is not readily apparent to an untrained individual, thereby reducing the possibility that the flow parameters of pump 10 can be changed by an unauthorized person. However, locking and unlocking of microcontroller 106 preferably entails a relatively simple combination of the controls of pump 10, thereby reducing the likelihood that an authorized person will forget how to lock/unlock microcontroller 106.

A method for infusing fluids into a patient in accordance with the method of the present invention entails providing a pump 10 as described herein. Programming of the flow parameters of pumping means 18 can be accomplished by the operation of operational control 23 and magnitude control 27. After the selected flow parameters have been programmed, an operator can "lock" microcontroller 106 by activating the pump controls in a predetermined pattern, as above-discussed. In the preferred embodiment of the present invention, microcontroller 106 is locked by simultaneously activating increase control 26 and decrease control 28 when dial control 24 is in Set Rate activated position 34.

When an operator wishes to place pump 10 in a "hold" condition, dial control 24 is rotated to Hold activated position 40, thereby causing microcontroller 106 to disable pumping means 18. In the preferred embodiment of the present invention, pump 10 can be placed in a "hold" condition when microcontroller 106 is locked. Upon rotation of dial control 24 to Hold activated position 40, "H 5" will appear on display screen 30, indicating that the default hold duration of five minutes has been set on timer subsystem 112. If the operator of pump 10 wishes to vary the hold duration from the default hold duration, magnitude control 27 is used selectively to increase or decrease the hold duration. When the selected hold duration has been reached, the operator is free to tend to whatever adjustments, activities, or treatments are required, although adjustments to the flow parameters of pump 10 cannot be effected if microcontroller 106 is in a locked condition. As the operator tends to these tasks, display screen 30 will display a countdown (in minutes) of the time remaining in the selected hold duration. Upon expiration of the selected hold duration, microcontroller 106 activates alarm 46, thereby causing alarm 46 to sound an audible alarm, and causes display screen 30 to display an appropriate alarm message. In the preferred embodiment of the present invention, display screen 30 displays "SEL run" when alarm 46 is activated, thereby informing the operator that the hold duration has expired and that pump 10 should again be placed in an activated state. The operator can disable alarm 46 by rotating dial control 24 from Hold activated setting 40.

As above-discussed, in the preferred embodiment of the present invention, microcontroller 106 is unlocked by simultaneously activating increase control 26 and decrease control 28 when dial control 24 is in the Set Rate activated position.

Although the apparatus and method of the present invention have been described herein with respect to certain preferred embodiments, it will be apparent to one of ordinary skill in the art that various modifications can be made to the present invention without departing from the intended spirit and scope of the invention, as claimed in the appended claims.

What is claimed is:

1. A method for controlling a flow parameter of a pump, said method comprising the steps of:

providing a pump, said pump comprising:
   a pumping means for pumping fluid, said pumping means having at least one flow parameter;
   a control means for controlling said at least one flow parameter of said pumping means, said control means coupled to said pumping means; and
   a control panel coupled to said control means, said control panel having a plurality of controls operable by a human, said control means being programmable by operation of said plurality of controls, whereby said at least one flow parameter of said pumping means is programmed by a human by operation of said plurality of controls;
   said control means having a lock, said lock being activated by activation of at least two of said plurality of controls, said control means preventing alteration of said at least one flow parameter when said lock is activated;

programming said at least one flow parameter of said pumping means by operating said plurality of controls;

activating said lock by activating at least two of said plurality of controls, thereby preventing alteration of said at least one flow parameter of said pumping means until said lock is deactivated.

2. A method for controlling a flow parameter of a pump in accordance with claim 1, wherein said plurality of controls comprises a magnitude increase control and a magnitude decrease control, and wherein said lock is activated by simultaneously activating said magnitude increase control and said magnitude decrease control.

3. A method for controlling a flow parameter of a pump in accordance with claim 2, wherein said controls further comprise a selector having a set rate setting, and wherein said method further comprises placing said selector in said set rate setting prior to simultaneously activating said magnitude increase control and said magnitude decrease control.

4. A method for controlling a flow parameter of a pump in accordance with claim 1, wherein said method further comprises deactivating said lock by activating at least two of said plurality of controls and reprogramming said at least one flow parameter of said pumping means by operating said plurality of controls.

5. A pump for infusing fluid into a human, said pump comprising:

a pumping means for pumping fluid, said pumping means having at least one flow parameter;
   a control panel having a plurality of controls operable by a human;
   a control means for controlling said at least one flow parameter of said pumping means, said control means coupled to said pumping means, said control means coupled to said plurality of controls, said control means further comprising a means for preventing alteration of said at least one flow parameter of said pumping means, said means for preventing alteration of said at least one flow parameter being activated by operation of at least two of said plurality of controls.

6. A pump for infusing fluid into a human in accordance with claim 5, wherein said plurality of controls comprises a magnitude increase control and a magnitude decrease control, and wherein said means for preventing alteration of said at least one flow parameter is activated by simultaneous operation of said magnitude increase control and said magnitude decrease control.

7. A pump for infusing fluid into a human in accordance with claim 6, wherein said plurality of controls further comprises a selector having a set rate position, and wherein said means for preventing alteration of said at least one flow parameter is activated by simultaneous operation of said magnitude increase control and said magnitude decrease control when said selector is in said set rate position.

8. A pump for infusing fluid into a human in accordance with claim 6, wherein said means for preventing alteration of said at least one flow parameter is deactivated by simultaneous operation of said magnitude increase control and said magnitude decrease control.

9. A pump for infusing fluid into a human in accordance with claim 5, wherein said means for preventing alteration of said at least one flow parameter is deactivated by operation of at least two of said plurality of controls.

* * * * *